United States Patent
Kataoka et al.

(10) Patent No.: US 11,324,835 B2
(45) Date of Patent: May 10, 2022

(54) NUCLEIC ACID-LOADED UNIT POLYION COMPLEX

(71) Applicants: THE UNIVERSITY OF TOKYO, Tokyo (JP); KAWASAKI INSTITUTE OF INDUSTRIAL PROMOTION, Kawasaki (JP)

(72) Inventors: Kazunori Kataoka, Kawasaki (JP); Kanjiro Miyata, Tokyo (JP); Shigeto Fukushima, Kawasaki (JP); Kotaro Hayashi, Kawasaki (JP); Sumiyo Watanabe, Tokyo (JP); HyunJin Kim, Tokyo (JP); Kazuko Toh, Kawasaki (JP)

(73) Assignees: KAWASAKI INSTITUTE OF INDUSTRIAL PROMOTION, Kawasaki (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/642,993

(22) PCT Filed: Aug. 30, 2018

(86) PCT No.: PCT/JP2018/032040
§ 371 (c)(1),
(2) Date: Feb. 28, 2020

(87) PCT Pub. No.: WO2019/044937
PCT Pub. Date: Mar. 7, 2019

(65) Prior Publication Data
US 2020/0197527 A1 Jun. 25, 2020

(30) Foreign Application Priority Data
Aug. 31, 2017 (JP) .............................. JP2017-166735

(51) Int. Cl.
| | | |
|---|---|---|
| *A61K 47/64* | (2017.01) | |
| *A61K 47/34* | (2017.01) | |
| *A61K 9/10* | (2006.01) | |
| *C12N 15/113* | (2010.01) | |
| *A61K 48/00* | (2006.01) | |

(52) U.S. Cl.
CPC ............ *A61K 47/6455* (2017.08); *A61K 9/10* (2013.01); *A61K 47/34* (2013.01); *C12N 15/1137* (2013.01); *A61K 48/00* (2013.01); *C12N 2310/14* (2013.01); *C12N 2310/351* (2013.01)

(58) Field of Classification Search
CPC .. A61K 47/34; A61K 47/6455; A61K 31/713; A61K 48/00; C12N 2310/351; C12N 15/113
See application file for complete search history.

(56) References Cited

U.S. PATENT DOCUMENTS

| | | |
|---|---|---|
| 7,642,343 B2 | 1/2010 | Nagasaki et al. |
| 7,780,957 B2 | 8/2010 | Kataoka et al. |
| 7,829,657 B2 | 11/2010 | Kataoka et al. |
| 8,318,205 B2 | 11/2012 | Kataoka et al. |
| 8,431,545 B2 | 4/2013 | Kataoka et al. |
| 8,546,487 B2 | 10/2013 | Kataoka et al. |
| 8,592,385 B2 | 11/2013 | Kataoka et al. |
| 8,668,933 B2 | 3/2014 | Hori et al. |
| 8,791,086 B2 | 7/2014 | Kataoka et al. |
| 8,822,213 B2 | 9/2014 | Stayton et al. |
| 8,853,167 B2 | 10/2014 | Kato et al. |
| 9,114,177 B2 | 8/2015 | Kataoka et al. |
| 9,278,075 B2 | 3/2016 | Kataoka et al. |
| 9,808,480 B2* | 11/2017 | Kataoka ............... A61K 47/645 |
| 2002/0016304 A1 | 2/2002 | Maruyama et al. |
| 2003/0148929 A1 | 8/2003 | Goto et al. |
| 2005/0260651 A1 | 11/2005 | Calias et al. |
| 2008/0249049 A1 | 10/2008 | Kataoka et al. |
| 2008/0305116 A1 | 12/2008 | Vlijmen et al. |
| 2009/0018216 A1 | 1/2009 | Kataoka et al. |
| 2009/0258416 A1 | 10/2009 | Kataoka et al. |

(Continued)

FOREIGN PATENT DOCUMENTS

| | | |
|---|---|---|
| EP | 0721776 A1 | 7/1996 |
| EP | 2415463 A1 | 2/2012 |

(Continued)

OTHER PUBLICATIONS

Harada et al. (European Journal of Pharmaceutical Sciences 13 (2001) 35-42). (Year: 2001).*
Communication from European Patent Office dated Nov. 30, 2015 in related EP application No. 13 782 198.8, including Search Opinion, Supplementary European Search Report and examined claims 1-9.
Communication from the European Patent Office dated Apr. 23, 2018 in related EP application No. 13 782 198.9, including Search Opinion and examined claims 1-13.

(Continued)

*Primary Examiner* — Anna R Falkowitz
(74) *Attorney, Agent, or Firm* — J-Tek Law PLLC; Jeffrey D. Tekanic; Scott T. Wakeman (57) ABSTRACT

A unit-type polyion complex for use in delivering nucleic acid to a target site in a patient includes one or more molecules of a block copolymer having a poly(ethylene glycol) segment and a cationic poly(amino acid) segment and one or more molecules of a nucleic acid. A total quantity of positive charges derived from side chains of the cationic poly(amino acid) segment of the block copolymer in the unit-type polyion complex is not offset by a total quantity of negative charges derived from the nucleic acid. Furthermore, the nucleic acid has a strand length of 10-50 bases, the molecular weight of the poly(ethylene glycol) segment is $40 \times 10^3$ or more, and the block copolymer has a binding constant (Ka) for the nucleic acid of $3.0 \times 10^5$ or more.

18 Claims, 3 Drawing Sheets

Specification includes a Sequence Listing.

(56) References Cited

U.S. PATENT DOCUMENTS

| | | |
|---|---|---|
| 2010/0121043 A1 | 5/2010 | Kataoka et al. |
| 2010/0221320 A1 | 9/2010 | Kato et al. |
| 2011/0052917 A1 | 3/2011 | Kataoka et al. |
| 2011/0123636 A1 | 5/2011 | Stayton et al. |
| 2011/0129921 A1 | 6/2011 | Johnson et al. |
| 2011/0142951 A1 | 6/2011 | Johnson et al. |
| 2011/0143434 A1 | 6/2011 | Stayton et al. |
| 2011/0143435 A1 | 6/2011 | Stayton et al. |
| 2011/0144017 A1 | 6/2011 | Dörwald |
| 2011/0229528 A1 | 9/2011 | Mirosevich et al. |
| 2011/0281354 A1 | 11/2011 | Stayton et al. |
| 2011/0281934 A1 | 11/2011 | Johnson et al. |
| 2011/0286957 A1 | 11/2011 | Prieve et al. |
| 2012/0014975 A1 | 1/2012 | Hegen et al. |
| 2012/0021514 A1 | 1/2012 | Johnson et al. |
| 2012/0053295 A1 | 3/2012 | Kataoka et al. |
| 2012/0076836 A1 | 3/2012 | Hori et al. |
| 2012/0076866 A1 | 3/2012 | Ishii et al. |
| 2012/0093881 A1 | 4/2012 | Kato et al. |
| 2012/0149649 A1 | 6/2012 | Kato et al. |
| 2012/0271034 A1 | 10/2012 | Liu et al. |
| 2013/0109743 A1 | 5/2013 | Kataoka et al. |
| 2014/0017328 A1 | 1/2014 | Kataoka et al. |
| 2014/0228516 A1 | 8/2014 | Stayton et al. |
| 2015/0051347 A1 | 2/2015 | Kataoka et al. |
| 2015/0080454 A1* | 3/2015 | Kataoka ............... A61K 48/00 514/44 A |
| 2016/0058703 A1 | 3/2016 | Ishii et al. |
| 2018/0042955 A1 | 2/2018 | Kataoka et al. |
| 2018/0153920 A1* | 6/2018 | Kataoka ............. A61K 47/6455 |
| 2018/0163208 A1 | 6/2018 | Kondo et al. |
| 2018/0334674 A1 | 11/2018 | Kondo et al. |
| 2019/0262378 A1 | 8/2019 | Akao |

FOREIGN PATENT DOCUMENTS

| | | |
|---|---|---|
| EP | 2415871 A1 | 10/2012 |
| EP | 2781536 A1 | 9/2014 |
| EP | 2842546 A1 | 3/2015 |
| EP | 3257515 A1 | 12/2017 |
| JP | 2000210079 A | 8/2000 |
| JP | 2008511290 A | 4/2008 |
| JP | 2011162512 A | 8/2011 |
| JP | 2010233499 A | 10/2011 |
| JP | 2012500793 A | 1/2012 |
| WO | 2005078084 A1 | 8/2005 |
| WO | 2006123631 A1 | 11/2006 |
| WO | 2007099660 A1 | 9/2007 |
| WO | 2007099661 A1 | 9/2007 |
| WO | 2010021770 A1 | 2/2010 |
| WO | 2010093036 A1 | 8/2010 |
| WO | 2010114013 A1 | 10/2010 |
| WO | 2009113645 | 11/2010 |
| WO | 2012005376 A1 | 1/2012 |
| WO | 2012096399 A1 | 7/2012 |
| WO | 2013162041 A1 | 10/2013 |
| WO | 2016129633 A1 | 8/2016 |
| WO | 2017086467 A1 | 5/2017 |
| WO | 2018079841 A1 | 5/2018 |

OTHER PUBLICATIONS

Zhao et al., N/P Ratio Significantly Influences the Transfection Efficiency and Cytotoxicity of a Polyethylenimine/Chitosan/DNA Complex, Biol. Pharm. Bull. 32(4) pp. 706-710 (2009).

Derouchey, J. et al., "Monomolecular Assembly of siRNA and Poly (ethylene glycol)-Peptide Copolymers", Biomacromolecules, 2008, vol. 9, No. 2, pp. 724-732, section "Synthesis of copolymers." of "Materials and Methods".

English translation of Written Opinion dated May 28, 2013 for related international application No. PCT/JP2013/062531.

English translation of International Search Report dated May 21, 2013 for related international application No. PCT/JP2013/062531.

English translation of the International Search Report dated May 26, 2017 for related international application No. PCT/JP2016/084328.

English translation of the International Search Report dated Nov. 20, 2019 for parent international application No. PCT/JP2018/032040.

Han,Y. et al., "Long Intergenic Non-Coding RNA TUGI is Overexpressed in Urothelial Carcinoma of the Bladder", J. Surg. Oncol., Apr. 1, 2013, vol. 107, No. 5, pp. 555-559.

Huang, M.D. et al., "Long non-coding RNA TUGI is up-regulated in hepatocellular carcinoma and promotes cell growth and apoptosis by epigenetically silencing of KLF2", Mol. Cancer, Aug. 4, 2015, vol. 14, No. 165, pp. 1-12.

Kano et al., "Grafting of poly(ethylene glycol) to poly-lysine augments its lifetime in blood circulation and accumulation in tumors without loss of the ability to associated with siRNA", 2011, Journal of Controlled Release, vol. 149, pp. 2-7.

Kim et al., "Precise Engineering of siRNA Delivery Vehicles to Tumors Using Polyion Complexes and Gold Nanoparticles", ACS Nano, vol. 8, No. 9, 2014, pp. 8979-8991.

Lee et al., "Di- and triblock siRNA-PEG copolymers: PEG density effect of polyelectrolyte complexes on cellular uptake and gene silencing efficiency", 2011, Macromolecular Bioscience, vol. 11, pp. 410-418.

Written Opinion of the International Searching Authority dated Feb. 21, 2017 for international application No. PCT/JP2016/084328, and machine translation thereof.

Maeda, Y. et al., "Synthesis and properties of cationic oligopeptides with different side chain lengths that bind to RNA duplexes, Bioorganic & Medicinal Chemistry", 2013, vol. 21, pp. 1717-1723.

Martinez et al., "Single-stranded antisense siRNAs guide target RNA cleavage in RNAi", Cell, 2002, vol. 110, pp. 563-574.

Nojima et al., "Lactoferrin conjugated with 40-kDa branched poly-(ethylene glycol) has an improved circulating half-life", 2009, Pharmaceutical Research, vol. 26, pp. 2125-2132.

Office Action from the Japanese Patent Office dated Mar. 29, 2017 in related Japanese application No. 2014-512733, and translation thereof.

Shimizu, H. et al., "siRNA-Based therapy ameliorates glomerulonephritis", J Am Soc Nephrol, 2010, vol. 21, No. 4, pp. 622-633.

Suma et al., "Enhanced stability and gene silencing ability of siRNA-loaded polyion complexes formulated from polyaspartamide derivatives with a repetitive array of amino groups in the side chain", Biomaterials 33, 2012, pp. 2770-2779.

Veronese et al., "PEGylation, successful approach to drug delivery", Drug Discovery Today, 2005, vol. 10, pp. 1451-1458.

English translation of the Written Opinion of the International Searching Authority in parent application No. PCT/JP2018/032040.

Xu,Y. et al., "Upregulation of the long noncoding RNA TUGI promotes proliferation and migration of esophageal squamous cell carcinoma", Tumor Biol., Mar. 2015, vol. 36, No. 3, pp. 1643-1651.

Zhang,E.B. et al., "P53-regulated long noncoding RNA TUGI affects cell proliferation in human non-small cell lung cancer, partly through epigenetically regulating HOXB7 expression", Cell Death Dis., May 22, 2014, vol. 5, No. e1243, pp. 1-12.

Zhang,Q. et al., "Down-regulation of Long Non-Coding RNA TUGI Inhibits Osteosarcoma Cell Proliferation and Promotes Apoptosis", Asian Pacific J. Cancer Prev., Apr. 2013, vol. 14, No. 4, pp. 2311-2315.

Anraku et al., "Living Unimodal Growth of Polyion Complex Vesicles via Two-Dimensional Supramolecular Polymerization", J. Am. Chem. Soc. vol. 135, pp. 1423-1429 (2013).

Harada et al., "Chain Length Recognition: Core-Shell Supramolecular Assembly from Oppositely Charged Block Copolymers", Science, vol. 283, pp. 65-67 (1999).

Hayashi, Doctoral Thesis, The University of Tokyo, 2016.

Supporting Information for Anraku et al., "Living Unimodal Growth of Polyion Complex Vesicles via Two-Dimensional Supramolecular Polymerization", J. Am. Chem. Soc. vol. 135, pp. 1423-1429 (2013).

(56) References Cited

OTHER PUBLICATIONS

Extended European Search Report from the European Patent Office dated Mar. 22, 2021 in counterpart EP application No. 18 851 853.4, including European Search Opinion and examined claims 1-8.

* cited by examiner

NUCLEIC ACID-LOADED UNIT POLYION COMPLEX

CROSS-REFERENCE

This application is the US national stage of International Patent Application No. PCT/JP2018/032040 filed on Aug. 30, 2018, which claims priority to Japanese Patent Application No. 2017-166735 filed on Aug. 31, 2017.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| TKU15218PCT_ST25.txt | Aug. 3, 2018 | 1 |

TECHNICAL FIELD

The present invention relates to a nucleic acid-loaded unit-type polyion complex and to a composition containing the unit-type polyion complex.

BACKGROUND OF THE INVENTION

Nucleic acid therapeutics can regulate various genes in cells, and hence are highly expected to be applied to various diseases, such as cancer and genetic disorders, which have heretofore been considered difficult to treat. However, because the in vivo stability of nucleic acid molecule is low, nucleic acid therapeutics require an appropriate technology for delivering the nucleic acid to target cells. For example, one known drug delivery technology for nucleic acids utilizes a block copolymer having a hydrophilic polymer segment and a cationic polymer segment to form a complex (polyion complex) with nucleic acid via electrostatic interactions.

Two examples of known polyion complexes are: (1) a polyion complex composed of an unspecified number of nucleic acids and an unspecified number of block copolymers, the block copolymers being radially arranged with their hydrophilic polymer segments directed outward and cationic polymer segments directed inward in a state of encapsulating the nucleic acids (hereinafter sometimes referred to as a "micelle-type polyion complex"); and (2) a polyion complex composed of a specific number of nucleic acids and a specific number of block copolymers, the polyion complex existing as a stable unit structure under in vivo conditions, for example, in the bloodstream (hereinafter sometimes referred to as a "unit-type polyion complex" or "uPIC") (for example, see Patent Document 1 mentioned below).

The unit-type polyion complex described in Patent Document 1 has a definite structure formed of a specific number of nucleic acids and a specific number of block copolymers, and can improve the blood retention properties of nucleic acids.

CITATION LIST

Patent Document 1: WO 2013/162041 A1

BRIEF SUMMARY OF THE INVENTION

To prepare the unit-type polyion complex described in Patent Document 1, the nucleic acids and/or the block copolymers must be carefully designed so that negative charges derived from the nucleic acids and positive charges derived from the block copolymers are offset to make the unit-type polyion complex electrically neutral.

It is one non-limiting object of the present teachings to provide a unit-type polyion complex that can be designed more simply.

According to one aspect of the present teachings, a unit-type polyion complex may include: a specific number of molecule(s) of a block copolymer having a poly(ethylene glycol) segment and a cationic poly(amino acid) segment; and a specific number of molecule(s) of a nucleic acid, wherein a total quantity of positive charges derived from side chains of the cationic poly(amino acid) segment of the block copolymer(s) in the unit-type polyion complex is not offset by a total quantity of negative charges derived from the molecule(s) of the nucleic acid, the strand length of the nucleic acid is 10-50 bases, the molecular weight of the poly(ethylene glycol) segment is $40 \times 10^3$ or more, and the block copolymer has a binding constant ($K_a$) for the nucleic acid of $3.0 \times 10^5$ or more.

In one embodiment, the unit-type polyion complex consists of two molecules of the block copolymer and one molecule of the nucleic acid.

In addition or in the alternative, the nucleic acid may be a double-stranded nucleic acid.

In addition or in the alternative, the molecular weight of the poly(ethylene glycol) segment may be $60 \times 10^3$ Da or more.

In addition or in the alternative, the poly(ethylene glycol) segment may be 2-chain branched, and the molecular weight of each of the poly(ethylene glycol) chains is $20 \times 10^3$ Da or more.

In addition or in the alternative, the cationic poly(amino acid) segment may contain one or more ornithine residues as a constituent amino acid or as constituent amino acids.

According to another aspect of the present teachings, a composition for nucleic acid delivery is provided that includes: any one of the above-described unit-type polyion complexes; and at least one additional block copolymer that is capable of forming the unit-type polyion complex, but which is in a free (unassociated) state (i.e. the at least one additional block copolymer is contained in the composition but is not associated with (bound to) the unit-type polyion complex composed of the one or more molecules of the block copolymer and the one or more molecules of the nucleic acid).

In one embodiment thereof, a ratio (N/P ratio) of a molar concentration of amino groups derived from the block copolymer and a molar concentration of phosphate groups derived from the nucleic acid in the composition is from 1 to 20.

In one or more embodiments the present teachings, a block copolymer having a predetermined affinity for a nucleic acid is used. As a result, surprisingly, a unit-type polyion complex (uPIC) that can improve the blood retention properties of the nucleic acid is obtained even though the charges of the block copolymer and the nucleic acid in the uPIC are not offset (not counterbalanced). Because it is not required to strictly control the negative charges derived from the nucleic acid and the positive charges derived from the block copolymer at the time of preparation, such a unit-type polyion complex can be designed more simply than known unit-type polyion complexes.

DETAILED DESCRIPTION OF THE INVENTION

A. Unit-type Polyion Complex

As was mentioned above, a unit-type polyion complex according to the present teachings may include: a specific number of molecule(s) of a block copolymer having a poly(ethylene glycol) segment and a cationic poly(amino acid) segment; and a specific number of molecule(s) of a nucleic acid. Preferably, the total quantity of positive charges derived from side chains of the cationic poly(amino acid) segment of the block copolymer(s) in the unit-type polyion complex is not offset by a total quantity of negative charges derived from the molecule(s) of the nucleic acid in the unit-type polyion complex (as a result, the unit-type polyion complex is not electrically neutralized, i.e. is not electrically neutral). Embodiments of the present teachings are described below, but the present invention is not limited to these embodiments. It is noted that the block copolymer and the nucleic acid to be used in practicing aspects of the present teachings, when obtained as a polymerization reaction product, may each exhibit a certain degree of polydispersity Therefore, in the present specification, when a mention is made about properties (such as molecular weight, degree of polymerization, and charge) of the block copolymer and properties (such as base length and charge) of the nucleic acid, such a mention should be understood as covering the average of an entire polymerization reaction product that exhibits polydispersity, unless otherwise specified. Therefore, for example, the charge quantity of the block copolymer is calculated on the basis of an average polymerization degree through the use of the degree of polymerization of cationic amino acid residues obtained by actual measurement as the average degree of polymerization. In addition, for example, an average molecular weight (e.g., number-average molecular weight) obtained by actual measurement may be applied as the molecular weight of the poly(ethylene glycol) segment.

A-1. First Embodiment

A-1-1. Overall Structure of a Unit-type Polyion Complex

Figure 1A:
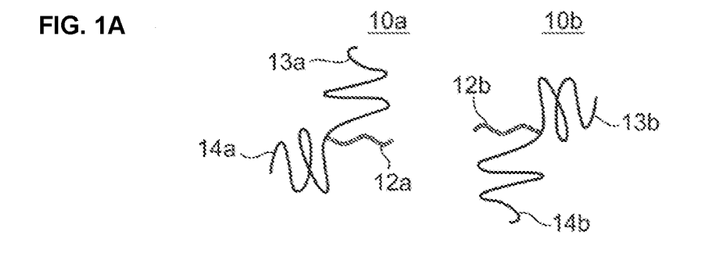
FIGS. 1(A)-1(D) are schematic views that illustrate the structure of a unit-type polyion complex, or components thereof, according to one embodiment of the present teachings.
Figure 1B:
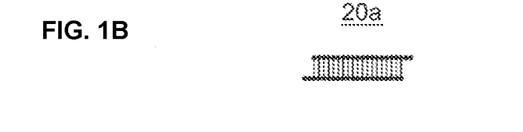
Figure 1C:
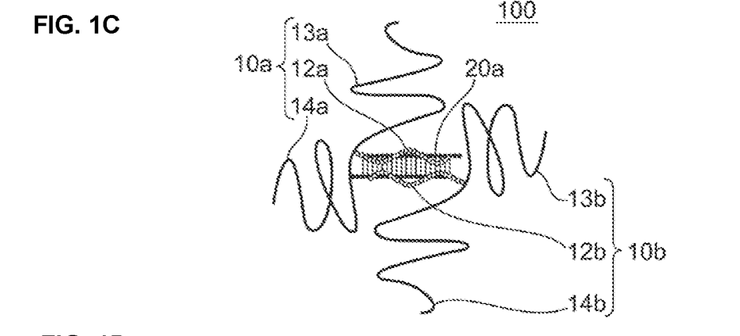
Figure 1D:
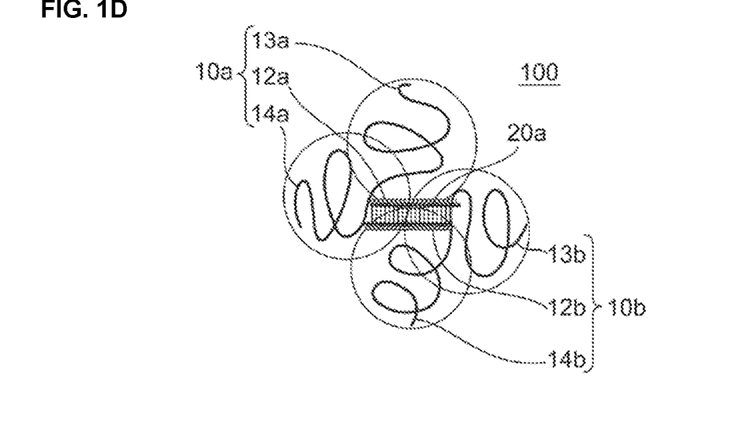

FIG. 1(A) to FIG. 1(D) are schematic views that illustrate an example of a uPIC according to a first embodiment of the present teachings. Specifically, FIG. 1(A) is a schematic view of two molecules of a block copolymer that may be used in the present teachings, FIG. 1(B) is a schematic view of one molecule of a nucleic acid that may be used in the present teachings, FIG. 1(C) is a schematic view of a uPIC consisting of the two block copolymers of FIG. 1(A) and the one nucleic acid molecule of FIG. 1(B), and FIG. 1(D) is a schematic view for illustrating the spatial extent of PEG segments in the uPIC of FIG. 1(C).

Block copolymers 10a and 10b illustrated in FIG. 1(A) have 2-chain branched PEG segments 13a and 14a, and 13b and 14b, respectively, and cationic poly(amino acid) segments 12a and 12b, respectively. In addition, the nucleic acid 20a illustrated in FIG. 1(B) is a double-stranded nucleic acid having an overhang of two bases at each end. The block copolymers 10a and 10b, and the nucleic acid 20a associate with each other through electrostatic interactions between positive charges derived from the cationic poly(amino acid) segments 12a and 12b and negative charges derived from the nucleic acid 20a, to thereby form a uPIC 100 (FIG. 1(C)). In the uPIC 100, the block copolymers 10a and 10b typically may be arranged opposite to each other in the main chain direction of the nucleic acid 20a. In such an arrangement, steric hindrance caused by mutual overlapping of the PEG segments 13a, 13b, 14a, and 14b can be minimized. As a result, even if the block copolymer has long-chain PEG segments that are branched, it can suitably form electrostatic bonds with the nucleic acid to form the uPIC. In addition, with such an arrangement, as illustrated in FIG. 1(D), the four PEG segments 13a, 13b, 14a, and 14b can extend so as to entirely cover the nucleic acid 20a, thereby being able to contribute to a high level of protection of the nucleic acid 20a. In one embodiment, the four PEG segments may be located so that the terminus of each of the PEG segments serves as a vertex of an approximately regular tetrahedron, and the nucleic acid may be located within the regular tetrahedron.

The uPIC according to this embodiment only needs to include a specific number of molecule(s) of the block copolymer and a specific number of molecule(s) of the nucleic acid, and is not limited to the structure of the illustrated example.

With regard to the uPIC according to this embodiment, in a physiological pH environment (pH=about 7.4), the quantity of positive charges derived from side chains of the cationic poly(amino acid) segment of the block copolymers is not offset by the quantity of negative charges from the nucleic acid, and as a result, the uPIC is not electrically neutralized (neutral). It is noted that, in the present specification, the description "the total quantity of positive charges derived from side chains of the cationic poly(amino acid) segment of the block copolymer(s) in the unit-type polyion complex is not offset by the total quantity of negative charges derived from the molecule(s) of the nucleic acid" or alternatively "the uPIC is not electrically neutralized (neutral)" means that the total charge quantity (absolute value) derived from the side chains of the cationic poly(amino acid) segments of all block copolymer molecule(s) contained in the uPIC is less than 90% or more than 110% of the total charge quantity (absolute value) derived from all nucleic acid molecule(s) contained in the uPIC. In the development of uPICs, hitherto, when positive charges derived from the side chains of the cationic poly(amino acid) segment and negative charges derived from the nucleic acid were not offset, there had been a concern that the uPIC may be brought into a charged state as a whole, thereby electrostatically attracting proteins or enzymes in blood, resulting in a reduction of blood retention properties, or the charged uPICs may further associate with each other or with the block copolymer and/or the nucleic acid, resulting in a reduction in uniformity (homogeneity). However, according to investigations by the present inventors, it has been found that even a charged uPIC can stably maintain its structure and have blood retention properties that excel by selecting a block copolymer having a predetermined affinity for the nucleic acid and using a long-chain PEG segment. In one embodiment, the total quantity of positive charges derived from the side chains of the cationic poly(amino acid) segments of all block copolymer molecule(s) in the uPIC in a physiological pH environment may be 45% or more and less than 90% (e.g., from 50% to 85%, or from 50% to 80%) of the total quantity of negative charges derived from all nucleic acid molecule(s) in the uPIC. In another embodiment, the total quantity of positive charges derived from the side chains of the cationic poly(amino acid) segments of the block copolymer(s) in the uPIC in a physiological pH environment may be more than 110% and 150% or less (e.g., from 115% to 140%) of the total quantity of negative charges derived from the molecule(s) of the nucleic acid.

Typically, uPICs of this embodiment have a smaller size than micelle-type PICs. The particle diameter (hydrodynamic diameter) of uPICs according to this embodiment is preferably from 10 nm to 30 nm, and may be, for example, from 10 nm to 25 nm, or for example, from 10 nm to 20 nm. Such a small size can contribute to delivering the nucleic acid contained in the uPIC to a deep part of a tissue.

A-1-2. Block Copolymer

Block copolymers that may be used in this embodiment include the PEG segment and the cationic poly(amino acid) segment, and may have a binding constant ($K_a$) of $3.0 \times 10^5$ or more, preferably $5.0 \times 10^5$ or more (e.g., $8.0 \times 10^5$ or more, $1.0 \times 10^6$ or more, $1.5 \times 10^6$ or more, or $2.0 \times 10^6$ or more) for the nucleic acid to be delivered. By using a block copolymer having the above-mentioned predetermined affinity for the nucleic acid, the block copolymer is less likely to dissociate from the uPIC in blood, or even if it dissociates, it can quickly re-associate; as a result, it is believed that, even in a state in which the negative charges derived from the nucleic acid and the positive charges derived from the block copolymer are not offset, the nucleic acid can be satisfactorily protected and high blood retention properties can be achieved. On the other hand, although the upper limit value of the binding constant ($K_a$) is not particularly limited, from the viewpoint of the ease of achievement, it may be, for example, $4.0 \times 10^6$ or less. In the present specification, block copolymers also include pharmaceutically acceptable salts of the block copolymers.

The binding constant ($K_a$) is measured by a method described below in the Examples. The binding constant ($K_a$) tends to increase as the number of electrostatic bonds between the cationic poly(amino acid) segment and the nucleic acid increases or as individual electrostatic bonds become stronger. Accordingly, the binding constant ($K_a$) may be controlled to fall within a desired range, for example, by adjusting the number of positive charges of the cationic poly(amino acid) segment, or by appropriately selecting the kinds of constituent amino acids of the cationic poly(amino acid) segment. It is noted that, when the structure of the block copolymer is fixed, it is considered that the binding constant ($K_a$) depends mainly on the quantity of negative charges of the nucleic acid. That is, as long as the base length of the nucleic acid remains the same, the binding constant does not substantially change in response to differences in the base sequence.

The PEG segment is preferably branched, more preferably 2-chain branched. Needless to say, the PEG segment also may be of a single-chain type that includes only one PEG chain.

The molecular weight of the PEG segment (in case the PEG segment is branched, the total of the molecular weights of respective PEG chains) is $40 \times 10^3$ Da or more, preferably $50 \times 10^3$ Da or more, more preferably $60 \times 10^3$ Da or more. In case the PEG segment is branched, the molecular weights of the respective PEG chains are not limited as long as the total of the molecular weights of all of the respective chains satisfies the above-mentioned range, and may be the same or different from each other. The molecular weight of each of the PEG chains of the branched PEG segment may be preferably $10 \times 10^3$ or more, for example, $20 \times 10^3$ or more, $25 \times 10^3$ or more, $30 \times 10^3$ or more, or $35 \times 10^3$ or more. It is preferred that each of the PEG chains of the branched PEG segment has a molecular weight of $20 \times 10^3$ or more, $25 \times 10^3$ or more, $30 \times 10^3$ or more, or $35 \times 10^3$ or more. Meanwhile, the molecular weights of the respective PEG chains may be independently, for example, $80 \times 10^3$ or less, $60 \times 10^3$ or less, or $50 \times 10^3$ or less. With the molecular weight of the PEG segment falling within such range, even when the uPIC is in a charged state, the nucleic acid can be suitably protected from enzymatic degradation and the like. In addition, the biocompatibility of the uPIC can be enhanced to prevent its decomposition or elimination as foreign matter. The molecular weight of the PEG segment may be determined by gel filtration chromatography (GFC) or the like, and in the determination, commercially available PEG having a known molecular weight (e.g., PEG for use as a molecular weight standard for GFC) may be used as a molecular weight marker.

The cationic poly(amino acid) segment may contain any appropriate basic amino acid as a constituent unit as long as the cationic poly(amino acid) segment has a desired positive charge in a physiological pH environment and the binding constant ($K_a$) of the block copolymer for the nucleic acid is $3.0 \times 10^5$ or more. The basic amino acid(s) is (are) preferably selected from lysine, ornithine, 2,3-diaminopropionic acid, and 2,4-diaminobutyric acid because these basic amino acids enable the desired binding constant to be easily achieved. Of those, ornithine is more preferred.

The ratio of the number of the at least one kind of basic amino acid (when two or more kinds of the basic amino acids are contained, the total number thereof) to the total number of all amino acid residues constituting the cationic poly(amino acid) segment may be preferably from 50% to 100%, and may be, for example, from 80% to 100%, from 90% to 100%, or 100%.

The cationic poly(amino acid) segment may further contain any other basic amino acid(s) as a constituent unit or constituent units as long as the desired binding constant is obtained. Examples of the other basic amino acid(s) include naturally-occurring basic amino acids, such as arginine and histidine, and amino acid derivatives obtained by introducing a cationic residue into the side chain of an acidic amino acid (e.g., Asp (DET) obtained by introducing an ethylenediamine structure into the side chain of aspartic acid).

The quantity of positive charges derived from the side chains of the cationic poly(amino acid) segment (per molecule of the block copolymer) may be appropriately set depending on, for example, the desired binding constant ($K_a$) for the nucleic acid, the structure of the uPIC, the quantity of negative charges of the nucleic acid, and the kind(s) of basic amino acid residue(s). The suitable range of the quantity of positive charges (per molecule of the block copolymer) may vary depending on, for example, the quantity of negative charges of the nucleic acid and the kind(s) of the basic amino acid residue(s), and hence the quantity of positive charges is not limited, but may be an integer of, for example, 9 or more, 10 or more, or 11 or more. Expressed in another manner, the quantity of positive charges (per molecule of the block copolymer), which is similarly not limited, may be 22.5% or more, 25% or more, or 27% or more of the quantity of negative charges of the nucleic acid. When such a quantity of positive charges is achieved through the use of the basic amino acid residue(s) (e.g., lysine, ornithine, 2,3-diaminopropionic acid, or 2,4-diaminobutyric acid), a block copolymer having a binding constant ($K_a$) for the nucleic acid that is equal to or higher than a predetermined value can be suitably obtained. On the other hand, if the quantity of positive charges is excessively large, the blood retention properties of the polymer itself may be reduced. Therefore, the quantity of positive charges may be preferably 50 or less, for example, 40 or less, 30 or less, or 25 or less.

The cationic poly(amino acid) segment may contain one or more non-basic amino acid residues (e.g., hydrophobic amino acid residue(s)) as long as the effect of the present teachings is obtained. The number of non-basic amino acid residues may be set to, for example, 10% or less, more preferably 5% or less, still more preferably 2% or less of the number of all amino acid residues constituting the cationic poly(amino acid) segment.

The PEG segment and the cationic poly(amino acid) segment are bound to each other via any appropriate linking group. Exemplary linking groups include an ester bond, an amide bond, an imino group, a carbon-carbon bond, an ether bond, and the like. In addition, these segments may be linked to each other via a linking group that is cleavable in vivo (such as a disulfide bond, a hydrazone bond, a maleamate bond, or an acetal group).

The PEG segment-side terminus and/or the cationic poly (amino acid) segment-side terminus of the block copolymer may be subjected to any appropriate modification as long as the effect of the present teachings is obtained. Exemplary modifications include the introduction of a protective group and the introduction of a target site-binding moiety.

The target site-binding moiety may be any appropriate moiety depending on the target tissue, the objective, or the like. The target site-binding moiety may be formed by conjugating a compound having the target site-binding moiety to the free terminus of the PEG segment of the block copolymer. It is noted, in the present specification, the target site-binding moiety refers to a moiety capable of binding specifically to substances derived from a living body and a virus to form a biological binding pair with the substances and having a biological recognition function. By introducing the target site-binding moiety, the reachability of the nucleic acid to the site(s) serving as the desired target(s) can be improved.

A preferred specific example of the block copolymer may be represented by the following general formula (1) or (2).

(1)

(2)

In each of the formulae, $R^{1a}$ to $R^{1d}$ each independently represent a hydrogen atom or an unsubstituted or substituted linear or branched alkyl group having 1 to 12 carbon atoms;

$R^2$ represents a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^3$ represents a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

L represents a divalent linking group or a valence bond;

x1 to x4 each independently represent an integer of from 455 to 1,800;

"z" represents an integer of from 9 to 50;

"w" represents an integer of from 1 to 4; and

"l" and "m" each independently represent an integer of from 0 to 5.

In formula (1) or (2), L represents a divalent linking group or a valence bond. Any appropriate linking group may be utilized as the divalent linking group. For example, L may represent -$L^1$-$L^2$-$L^3$- in the formula (1) and L may represent -$L^4$-$L^5$-$L^6$- in the formula (2). In the formulae, $L^1$ and $L^4$ each independently represent —(O—(CH$_2$)$_a$)$_b$-$L^{1a}$- where "a" and "b" represent integers of from 1 to 5 and from 0 to 300, respectively, provided that it is not necessary that all "a"s be identical to each other when "b" represents 2 or more, and $L^{1a}$ represents a valence bond, —S—S—, —NH—, —O—, —O—CH(CH$_3$)—O—, —OCO—, —OCONH—, —NHCO—, —NHCOO—, —NHCONH—, —CONH—, or —COO—; $L^2$ and $L^5$ each independently represent a valence bond or -$L^{2a}$-$L^{2b}$-$L^{2c}$-, where $L^{2a}$ and $L^{2c}$ represent structures serving as spacers, an example thereof is, but not particularly limited to, a substituted or unsubstituted alkylene group having 1 to 12 carbon atoms, and $L^{2b}$ represents anyone of the structures represented by the following formulae (III) to (V); $L^3$ represents —((CH$_2$)$_c$—O)$_d$— (CH$_2$)$_e$-$L^{3a}$-, where "c", "d", and "e" represent integers of from 1 to 5, from 0 to 500, and from 0 to 5, respectively, provided that it is not necessary that all "c"s be identical to each other when "d" represents 2 or more; $L^{3a}$ represents —NH— or —O—; and $L^6$ represents —((CH$_2$)$_f$—O)$_g$—(CH$_2$)$_h$-$L^{6a}$-(CH$_2$)$_i$—CO—, where "f", "g", "h", and "i" represent integers of from 1 to 5, from 0 to 300, from 0 to 5, and from 0 to 5, respectively, provided that it is not necessary that all "f"s be identical to each other when "g" represents 2 or more, and $L^{6a}$ represents —OCO—, —NHCO—, —OCONH—, —NHCOO—, —NHCONH—, —CONH—, or —COO—.

(III)

(IV)

(V)

Alkyl moieties in the linear or branched alkyloxy group, the alkyl-substituted imino group, and the alkyl group having 1 to 12 carbon atoms, which are defined by groups $R^{1a}$ to $R^{1d}$, $R^2$, and $R^3$, may be, for example, a methyl group, an ethyl group, a n-propyl group, an isopropyl group, a n-butyl group, a sec-butyl group, a tert-butyl group, a n-hexyl group, a decyl group, or an undecyl group. Alkenyl or alkynyl moieties in the linear or branched alkenyloxy group having 2 to 12 carbon atoms or in the linear or branched alkynyloxy group having 2 to 12 carbon atoms may be exemplified by an alkenyl or alkynyl moiety including a double bond or a triple bond in the alkyl group having 2 or more carbon atoms as exemplified above.

For such group or moiety, substituents in cases that have been "substituted" may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkylsiloxy group, a siloxy group, or a silylamino group, or may be exemplified by an acetalized formyl group, a formyl group, or a halogen atom, such as chlorine or fluorine. In this context, for example, the expression "$C_{1-6}$" means 1 to 6 carbon atoms and is used with the same meaning in the following description. Furthermore, an unsubstituted or substituted linear or branched alkyl moiety having 1 to 12 carbon atoms in the unsubstituted or substituted linear or branched alkylcarbonyl group having 1 to 24 carbon atoms may be selected with reference to the examples, and an alkyl moiety having 13 or more carbon atoms may be, for example, a tridecyl group, a tetradecyl group, a pentadecyl group, a nonadecyl group, a docosanyl group, or a tetracosyl group. In addition, the substituent(s) may be a group containing a target site-binding moiety.

Symbol "z" is set so that, when the uPIC is formed, the total quantity of positive charges derived from the side chains of the cationic poly(amino acid) segment of the block copolymer(s) is less than 90% or more than 110% of the total quantity of negative charges derived from the molecule(s) of the nucleic acid. In addition, "z" may be set so that the binding constant ($K_a$) for the nucleic acid is equal to or higher than a predetermined value. Although it may vary depending on the value of "w", the negative charge number of the nucleic acid, or the like, when "z" represents, for example, an integer of 22.5% or more, 25% or more, or 27% or more, of the quantity of negative charges of the nucleic acid, a block copolymer having a binding constant ($K_a$) equal to or higher than a predetermined value for the nucleic acid can be suitably obtained. Similarly, although it may vary depending on the value of "w", the number of negative charges of the nucleic acid, or the like, when "z" represents an integer of 9 or more, for example, an integer of 10 or more or an integer of 11 or more, a block copolymer having a binding constant ($K_a$) equal to or higher than a predetermined value for the nucleic acid can be suitably obtained. The upper limit of "z" may be, for example, an integer of 40 or less or an integer of 30 or less.

Symbol "w" preferably represents an integer of from 1 to 3 from the viewpoint of increasing the binding constant for the nucleic acid, and further, more preferably represents 3 from the viewpoint of the ease of production. For example, when "z" represents 14 or less, in particular, 13 or less, "w" preferably represents an integer of from 1 to 3, for example, 3. For "w", the same group may be selected for all repeating units including these groups, or different groups may be selected for the respective repeating units. When different groups are selected, the respective repeating units are bound to each other in any suitable order, and may form a random structure or a block structure.

Symbols x1 to x4, which represent the numbers of repeats of ethylene glycol, each independently represent, as a lower limit, for example, 600, or for example, 700, or for example, 800, and as an upper limit, for example, 1,400, or for example, 1,200, or for example, 1,100.

A-1-3. Nucleic Acid

In the present specification, "nucleic acid" means a poly- or oligonucleotide that includes nucleotides composed of a purine or pyrimidine base, a pentose, and phosphoric acid. For example, a double-stranded nucleic acid, such as double-stranded oligo- or polyRNAs, double-stranded oligo- or polyDNAs, or double-stranded oligo- or poly(nucleic acid) s in which RNA and DNA exist in a mixed state in the same strand, may be preferably used. The nucleotides contained in the nucleic acids may be of a natural type or of a chemically modified non-natural type, or may have added thereto an amino group, a thiol group, a fluorescent compound, or any other molecule.

The strand length of the nucleic acid (in double-stranded nucleic acids, the length of the part constituting the double strand) may be typically 10-50 bases, for example, 10-30 bases.

Preferred examples of the nucleic acid may include functional nucleic acids, such as siRNA, miRNA mimic, shRNA, and a decoy nucleic acid.

The siRNA may be, for example, any siRNA designed for a target gene or polynucleotide by any appropriate method. Regarding the strand length of the siRNA, the part constituting a double strand may have a length of preferably from 15 bases to 50 bases, more preferably from 18 bases to 30 bases, and it includes compounds known in the art and all nucleotides having actions or functions similar to those of the above-described compounds. Specific examples of the siRNA include, but are not limited to, ones that may be designed with reference to a gene to be targeted by gene therapy.

A-2. Second Embodiment

According to a second embodiment of the present teachings, a unit-type polyion complex is provided that includes: a specific number of molecule(s) of a block copolymer having a poly(ethylene glycol) segment and a cationic poly(amino acid) segment; and a specific number of molecule(s) of a nucleic acid, wherein a total quantity of positive charges derived from side chains of the cationic poly(amino acid) segment of the block copolymer(s) is not offset by a total quantity of negative charges derived from the molecule(s) of the nucleic acid, the strand length of the nucleic acid is 10-50 bases, the molecular weight of the poly(ethylene glycol) segment is $40 \times 10^3$ Da or more, and the block copolymer has a predetermined binding constant ($K_a$) for a double-stranded nucleic acid (provided that a phosphate group is not appended to the 5' end of each of the strands) composed of the sense strand set forth in SEQ ID NO: 1 and the antisense strand set forth in SEQ ID NO: 2.

In uPICs according to this embodiment, the total quantity of positive charges derived from side chains of the cationic poly(amino acid) segment of the block copolymer(s) in a physiological pH environment is not offset by the total quantity of negative charges derived from the one or more molecules of the nucleic acid, and as a result, the uPIC is not electrically neutralized (neutral). The total quantity of positive charges derived from the side chains of the cationic poly(amino acid) segments of all block copolymer molecule(s) in the uPIC in a physiological pH environment may be 45% or more and less than 90% (e.g., from 50% to 85%, or from 50% to 80%), or more than 110% and 150% or less (e.g., from 115% to 140%) of the total quantity negative charges derived from all nucleic acid molecule(s) in the uPIC.

The block copolymer may have a binding constant ($K_a$) of, for example, $3.0 \times 10^5$ or more, preferably $5.0 \times 10^5$ or more (e.g., $8.0 \times 10^5$ or more, $1.0 \times 10^6$ or more, $1.5 \times 10^6$ or more, or $2.0 \times 10^6$ or more) for the double-stranded nucleic acid (provided that a phosphate group is not appended to the 5' end of each of the strands) composed of the sense strand set forth in SEQ ID NO: 1 and the antisense strand set forth in SEQ ID NO: 2. The binding constant ($K_a$) for the double-stranded nucleic acid may be set to, for example, $4.0 \times 10^6$ or less. Such block copolymers exhibit high affinities for short-strand nucleic acids of a length of about 10-50 bases, and can suitably associate therewith to form uPICs. For example, the block copolymers described in Section A-1-2 may be used as the block copolymer.

For example, the nucleic acids described in Section A-1-3 may be used as the nucleic acid. In uPICs according to this embodiment, single-stranded nucleic acids (e.g., single-stranded oligo- or polyRNAs, single-stranded oligo- or polyDNAs, or single-stranded oligo- or poly(nucleic acid) s in which RNA and DNA exist in a mixed state) preferably may be used as well as double-stranded nucleic acids. Specific examples of a single-stranded nucleic acid having a strand length of from 10-50 bases may preferably include functional nucleic acids, such as micro RNAs, antisense nucleic acids, aptamers, and ribozymes. When a single-stranded nucleic acid is used, uPICs according to the second embodiment may be a uPIC consisting of one molecule of the nucleic acid and one molecule of the block copolymer or a uPIC consisting of one molecule of the nucleic acid and two molecules of the block copolymer.

B. Method of Preparing a Unit-type Polyion Complex

For example, uPICs of the present teachings may be prepared by mixing any appropriate block copolymer and any appropriate nucleic acid in an aqueous solution buffered as needed (e.g., phosphate buffered saline or HEPES buffer).

C. Composition for Nucleic Acid Delivery

A composition for nucleic acid delivery of the present teachings includes: any one of the uPICs described in Section A above; and at least one additional unassociated block copolymer that is capable of forming the uPIC, but is in a free state. According to this composition for nucleic acid delivery, blood retention properties of the nucleic acid can be increased as compared to using the uPIC alone (i.e. without free or unassociated (excess) block copolymer(s)). The reason why such effect is obtained is believed to be, for example, as described below. That is, in a solution containing the uPIC, dissociation and association between the nucleic acid and the block copolymer occur as a reversible reaction, and as a result, uPICs reversibly decompose and reform. Accordingly, by admixing excess unassociated block copolymer in a free state with the uPICs, the equilibrium can be shifted towards association, and as a result of this, the nucleic acid can be more suitably protected than when uPICs are administered alone without excess block copolymer.

Any free (unassociated) block copolymer can be used as long as it is capable of forming a uPIC with the nucleic acid by replacing block copolymer constituting the now-dissociated uPIC. Specific examples thereof are the block copolymers described in Section A-1-2 above, and a preferred example thereof is a block copolymer identical to (having the same composition as) the block copolymer forming the uPIC. Such a block copolymer has a high affinity for the nucleic acid, and hence can suitably reassociate with the nucleic acid even in the bloodstream.

Such a composition for nucleic acid delivery may be obtained by mixing the block copolymer (e.g., an excess of the block copolymer) and the nucleic acid in an aqueous solution, which is buffered as needed, so as to achieve a desired N/P ratio. Herein, the N/P ratio means a ratio of the molar concentration of all amino groups derived from all of the block copolymers in the composition and (with respect to) the molar concentration of all phosphate groups derived from all of the molecules of the nucleic acid in the composition.

In such a composition for nucleic acid delivery, the N/P ratio is, for example, 1 or more, preferably 1.5 or more, more preferably 2 or more. In addition, the upper limit of the N/P ratio may be set to typically 20 or less, for example, 10 or less, 5 or less, or 4 or less. In such a composition for nucleic acid delivery, when a double-stranded nucleic acid is selected as the nucleic acid to be delivered and a block copolymer having a binding constant ($K_a$) of, for example, $8.0 \times 10^5$ or more, preferably $1.0 \times 10^6$ or more for the nucleic acid is used, even if the N/P ratio is 5 or less (e.g., about 3), 10% or more of the administered nucleic acid can still be retained (present) in the blood at 3 hours after intravenous administration.

EXAMPLES

In the following, although the present teachings are described more specifically by way of Examples, the present invention is not limited to these Examples. It is noted that, in the Examples below, polymer structures are specified in the order of the molecular weight (kDa) of the PEG and the degree of polymerization of the poly(amino acid). For example, when the molecular weight of each chain of a 2-chain branched PEG is 37 kDa and a cationic poly(amino acid) segment is composed of ten ornithine residues, the polymer is abbreviated as "PEG-pOrn (37×2-10)".

Preparation of Block Copolymer

By using 2-chain branched poly(ethylene glycol) derivatives having various molecular weights (manufactured by NOF Corporation), white powders of the following block copolymers (hydrochlorides) were obtained by the same method as the method for preparing block copolymers described in the Examples of Patent Document 1: PEG-pOrn (37×2-11), PEG-pOrn (37×2-14), PEG-pOrn (37×2-20), PEG-pOrn (37×2-40), PEG-pLys(37×2-9), PEG-pLys(37×2-14), PEG-pLys(37×2-20), and PEG-pLys(37×2-40). The degrees of polymerization of their poly(amino acid) segments were determined by $^1$H-NMR.

Example 1

PEG-pOrn (37×2-11) and siRNA were separately dissolved in 10 mM HEPES buffer (pH 7.3), and the resulting solutions were mixed so as to achieve a final concentration of the siRNA of 10 μM, and to achieve N/P ratios of 0.25, 0.5, 1, 2, 3, 5, or 10, to thereby prepare PIC solutions. As the siRNA, siLuc (siRNA against luciferase) having no phosphate group appended to the 5' end of each strand was used. If required for the particular experiment that was performed, the 5' end was labeled with Alexa647 or the like before use.

Base Sequence of siLuc:
Sense 5'-CUUACGCUGAGUACUUCGAdTdT-3' (SEQ ID NO: 1)
Antisense 5'-UCGAAGUACUCAGCGUAAGdTdT-3' (SEQ ID NO: 2)

Example 2

PIC solutions were prepared in the same manner as in Example except that PEG-pOrn (37×2-14) was used in place of PEG-pOrn (37×2-11).

Example 3

PIC solutions were prepared in the same manner as in Example except that PEG-pLys(37×2-14) was used in place of PEG-pOrn (37×2-11).

Comparative Example 1

PIC solutions were prepared in the same manner as in Example except that PEG-pLys(37×2-9) was used in place of PEG-pOrn (37×2-11).

Reference Example 1

PIC solutions were prepared in the same manner as in Example except that PEG-pLys(37×2-20) was used in place of PEG-pOrn (37×2-11). The uPIC solution (N/P ratio=10) obtained in Reference Example 1 is substantially equivalent to the uPIC solution disclosed as pharmaceutical preparation B in Table 2 of Patent Document 1, and contains uPICs that each consist of one molecule of the siRNA and two molecules of the block copolymer.

Structural Analysis of uPIC 1

The PIC solutions prepared in Examples 1 to 3 and Comparative Example 1 described above were each subjected to analytical ultracentrifugation according to a sedimentation equilibrium method (SE-AUC analysis) and fluorescence correlation spectroscopy analysis (FCS analysis) to determine the nucleic acid association number and the block copolymer association number per PIC. Specific methods are as described below.

SE-AUC Analysis

The SE-AUC analysis was carried out using a Beckman Optima XL-A ultracentrifugation system for analysis (manufactured by Beckman Coulter) that includes an absorbance measurement system. The PIC solutions prepared at an N/P ratio of 1 in Examples 1-3 and Comparative Example 1 described above were each diluted with 10 mM HEPES buffer (pH 7.4) containing 150 mM NaCl so as to have an siRNA concentration of 0.6 μM, thereby providing measurement samples. The measurement samples were each centrifuged at 20° C. for 72 hours, and then absorption at a wavelength of 260 nm was measured as a function of r. The measurement result of each of the samples was analyzed with ORIGIN® software to determine the molecular weight (Da) of the PIC.

FCS Analysis

The FCS analysis was carried out using a confocal laser scanning microscope (manufactured by Carl Zeiss, product name "LSM510") equipped with a 40× objective lens (C-Apochromat, manufactured by Carl Zeiss) and a ConfoCor3 module. The PIC solutions prepared at an N/P ratio of 1 in the Examples and Comparative Example described above were each diluted with 10 mM HEPES buffer (pH 7.4) containing 150 mM NaCl so as to have an siRNA concentration of 100 nM, thereby providing measurement samples. The measurement samples were transferred to an 8-well chamber and subjected to FCS measurement with a sampling time of 15 seconds. The measurement was repeated 5 times. The measurement results were analyzed using the ConfoCor3 software to determine the average number of fluorescent particles within a measurement area. Subsequently, the nucleic acid association number per PIC was determined through calculation by using the following equation (a).

$$AN_{siRNA} = N_{siRNA}/N_{PIC} \quad (a)$$

In equation (a) $AN_{siRNA}$ represents the nucleic acid association number per PIC, $N_{siRNA}$ represent the average number of fluorescent particles of a control sample containing only fluorescence-labeled siRNA and $N_{PIC}$ represents the average number of fluorescent particles of a measurement sample derived from a PIC solution.

The molecular weight (Da) of the PIC and the nucleic acid association number per PIC were substituted into the following equation (b) to calculate the block copolymer association number per PIC.

$$AN_{copolymer} = [MW_{PIC} - (MW_{siRNA} \times AN_{siRNA})]/MW_{copolymer} \quad (b)$$

In equation (b) $AN_{copolymer}$ represents the block copolymer association number per PIC, $MW_{PIC}$ represents the molecular weight (Da) of the PIC obtained in the SE-AUC analysis, and $MW_{siRNA}$ and $MW_{copolymer}$ represent the molecular weights (Da) of the siRNA and the block copolymer calculated on the basis of their structural formulae, respectively.

The results of the structural analysis are shown in Table 1.

TABLE 1

| | Polymer used | Molecular weight of PIC (kDa) | siRNA association number | Polymer association number | Charges of polymer side chains/nucleic acid charges* (%) |
|---|---|---|---|---|---|
| Example 1 | PEG-pOrn(37 × 2 – 11) | 180 | 1.0 ± 0.1 | 2.2 ± 0.1 | 55 |
| Example 2 | PEG-pOrn(37 × 2 – 14) | 148 | 1.0 ± 0.1 | 1.8 ± 0.1 | 70 |
| Example 3 | PEG-pLys(37 × 2 – 14) | 160 | 1.0 ± 0.1 | 1.9 ± 0.1 | 70 |
| Comparative Example 1 | PEG-pLys(37 × 2 – 9) | 169 | 1.1 ± 0.1 | 2.0 ± 0.1 | 45 |

*The ratio of charges derived from polymer side chains to charges derived from the nucleic acid was calculated assuming that the nucleic acid association number per PIC is 1 and the polymer association number is 2

As shown in Table 1, the siRNA association number and the block copolymer association number determined by actually performing FCS and SE-AUC analyses are about 1 and about 2, respectively. In this connection, the fact that the standard deviation of each association number is 0.1 or less shows that the PICs obtained in Examples 1 to 3 and Comparative Example 1 each have extremely high structural homogeneity and have a specific uniform structure. In view of the foregoing, it is logically understood that the PICs prepared in Examples 1 to 3 and Comparative Example 1 are uPICs that each consist of one molecule of siRNA and two molecules of block copolymer.

Structural Analysis of uPIC 2

The uPIC solutions obtained in Reference Example 1 described above were subjected to FCS analysis in the same manner as in the "Structural Analysis of uPIC 1" above to determine the nucleic acid association number per PIC and the average particle diameter (hydrodynamic diameter: $D_H$) of the PIC. The average particle diameter ($D_H$) of the PIC was calculated using the ConfoCor3 module by: converting an autocorrelation curve obtained in the FCS measurement into a diffusion time; then converting the diffusion time into a diffusion coefficient ($D_C$) with the use of a Cy5 dye as a control; and substituting the diffusion coefficient into Einstein's relationship (Stokes-Einstein equation). The results are shown in FIG. 2.

Figure 2:
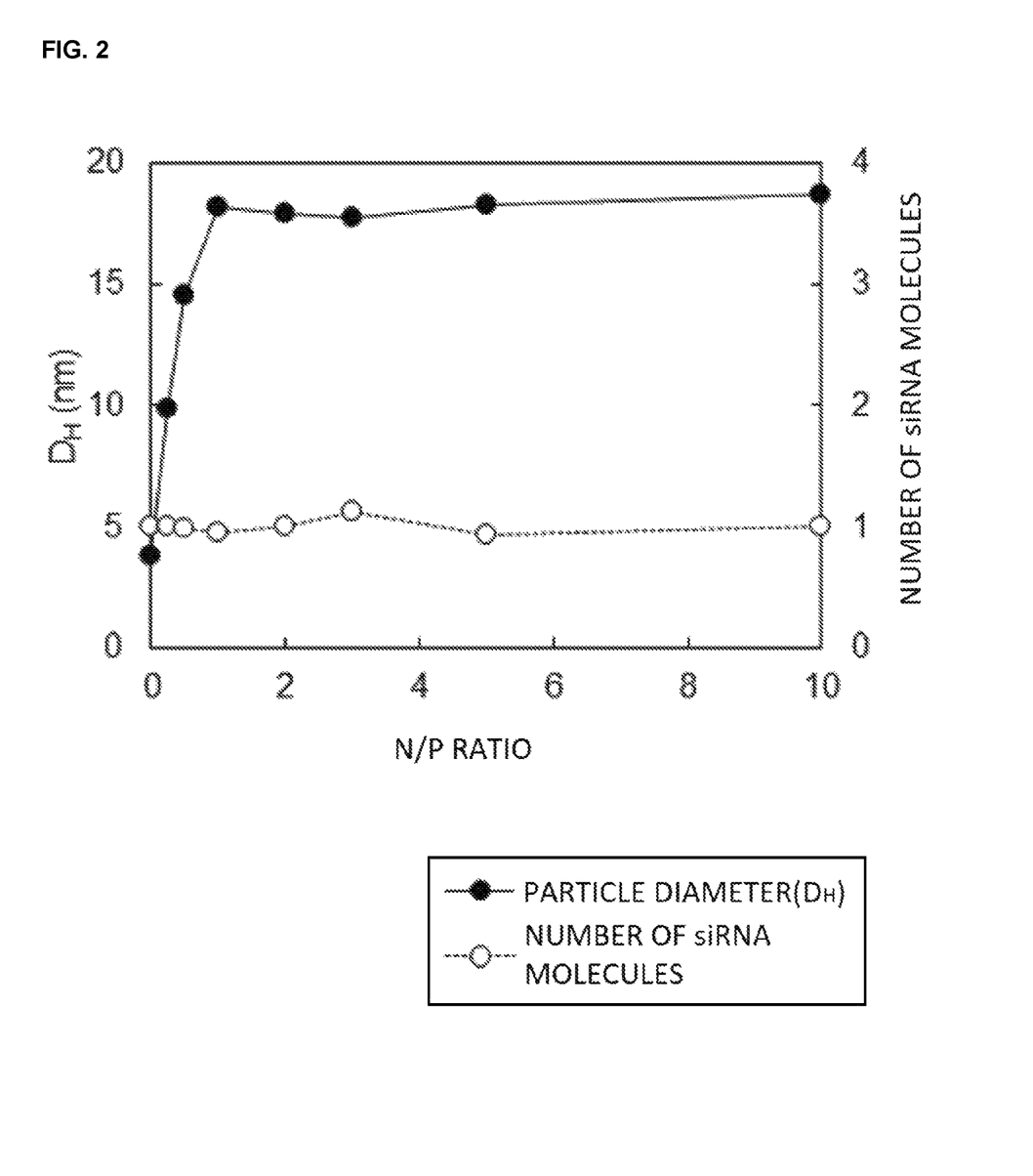
FIG. 2 is a graph that shows average particle diameters of unit-type polyion complexes and a nucleic acid association number in the unit-type polyion complexes.

As shown in FIG. 2, the uPIC solutions of Reference Example 1 had average uPIC particle diameters of about 18 nm and nucleic acid association numbers of about 1, both of which were nearly constant over the N/P ratio range of from 1 to 10. In view of this, it is understood that the uPIC of Reference Example 1 is present as a stable unit structure, without forming a secondary association between the uPICs or with a free (additional) block copolymer.

Measurement of the Binding Constant

The binding constant ($K_a$) of each of the block copolymers obtained above for siRNA was determined by the following method. The results are shown in Table 2.

The binding constant was determined by quantifying the intensity of fluorescence enhanced by the binding of ethidium bromide (EtBr) to the nucleic acid in competitive binding of EtBr and the block copolymer to siRNA. The fluorescent intensity was quantified using a spectrofluorometer (manufactured by JASCO Corporation, model no. FP-6600). Specifically, the block copolymer serving as a measurement object and the siRNA (siLuc used in the Examples and Comparative Example, without the Alexa647 label) were separately dissolved in 10 mM HEPES buffer (pH 7.3) containing 150 mM NaCl, and the resulting solutions were mixed so as to achieve a final concentration of the siRNA of 1 μM, and to achieve an N/P ratio of 0.25, 0.5, or 1, to thereby prepare PIC solutions. To 1 mL of the PIC solution at each N/P ratio, an about 0.5 mM aqueous solution of EtBr was added dropwise 10 times in amounts of 10 μL, and the fluorescent intensity (ex 525 nm, em 600 nm) was measured after each time of dropwise addition. The binding constant was calculated by analyzing the resultant fluorescent intensities based on a previously reported method (J. Chem. Edu. 71, 77 (1994)).

TABLE 2

| Block copolymer | Binding constant (Ka) |
|---|---|
| PEG-pOrn(37 × 2 – 11) | $1.1 \times 10^6$ |
| PEG-pOrn(37 × 2 – 14) | $2.3 \times 10^6$ |
| PEG-pOrn(37 × 2 – 20) | $2.1 \times 10^6$ |
| PEG-pOrn(37 × 2 – 40) | $2.3 \times 10^6$ |
| PEG-pLys(37 × 2 – 9) | $1.0 \times 10^5$ |
| PEG-pLys(37 × 2 – 14) | $4.0 \times 10^5$ |
| PEG-pLys(37 × 2 – 20) | $4.2 \times 10^5$ |
| PEG-pLys(37 × 2 – 40) | $4.2 \times 10^5$ |
| Reference: EtBr*[1] | $6.4 \times 10^5$ |

*[1] value measured using naked siRNA in place of PIC

Evaluation of Blood Retention Properties of siRNA 1

The uPIC solutions (N/P ratio=1) obtained in Examples 1-3, Comparative Example 1, and Reference Example 1 were respectively administered to the tail veins of 6-week-old female BALB/c mice. At this time, the administration was carried out so that the dose was 2 nmol/mouse of siLuc. After that, fluorescent intensities attributed to siLuc in the blood vessels in the ears of the mice were measured over time using an in vivo confocal imaging system (Nikon A1R, manufactured by Nikon Corporation), and relative fluorescent intensities were determined according to the following equation (n=1). Relative fluorescent intensities obtained immediately after the administration, after 5 minutes, after 10 minutes, after 30 minutes, and after 60 minutes are shown in Table 3.

Relative fluorescent intensity (%)=(intensity at the measurement time−background intensity)/(maximum intensity−background intensity)×100

TABLE 3

| | Polymer used | Relative fluorescent intensity (%) | | | | |
|---|---|---|---|---|---|---|
| | | Immediately after administration | After 5 minutes | After 10 minutes | After 30 minutes | After 60 minutes |
| Example 1 | PEG-pOrn (37 × 2 – 11) | 100 | 96 | 84 | 82 | 58 |
| Example 2 | PEG-pOrn (37 × 2 – 14) | 100 | 96 | 84 | 63 | 34 |
| Example 3 | PEG-pLys (37 × 2 – 14) | 100 | 78 | 66 | 27 | 14 |
| Comparative Example 1 | PEG-pLys (37 × 2 – 9) | 100 | (Unevaluable) | (Unevaluable) | (Unevaluable) | (Unevaluable) |
| Reference Example 1 | PEG-pLys (37 × 2 – 20) | 100 | 73 | 48 | 23 | 9 |

As shown in Table 3, the uPIC solutions of Examples 1 to 3 each exhibited blood retention properties of the nucleic acid that were comparable to or higher than the uPIC solution of Reference Example 1. In particular, each of Examples 1 and 2 used a block copolymer having a binding constant ($K_a$) for the nucleic acid of more than $1.0 \times 10^6$. As a result, the blood retention properties of the nucleic acid were greater than Reference Example 1. On the other hand, with regard to the uPIC solution of Comparative Example 1, the fluorescent intensity significantly reduced immediately after the administration, and stable measurement was not possible thereafter.

Evaluation of Blood Retention Properties of siRNA 2

In the same manner as in the Evaluation of Blood Retention Properties of siRNA 1 above, except for using the uPIC solutions at an N/P ratio of 10, the uPIC solutions were respectively administered to the tail veins of 6-week-old female BALB/c mice, fluorescent intensities attributed to siLuc in the bloodstream in the ears of the mice were measured over time, and relative fluorescent intensities were determined (n=1). Changes over time in relative fluorescent intensity are shown in FIG. 3.

Figure 3:
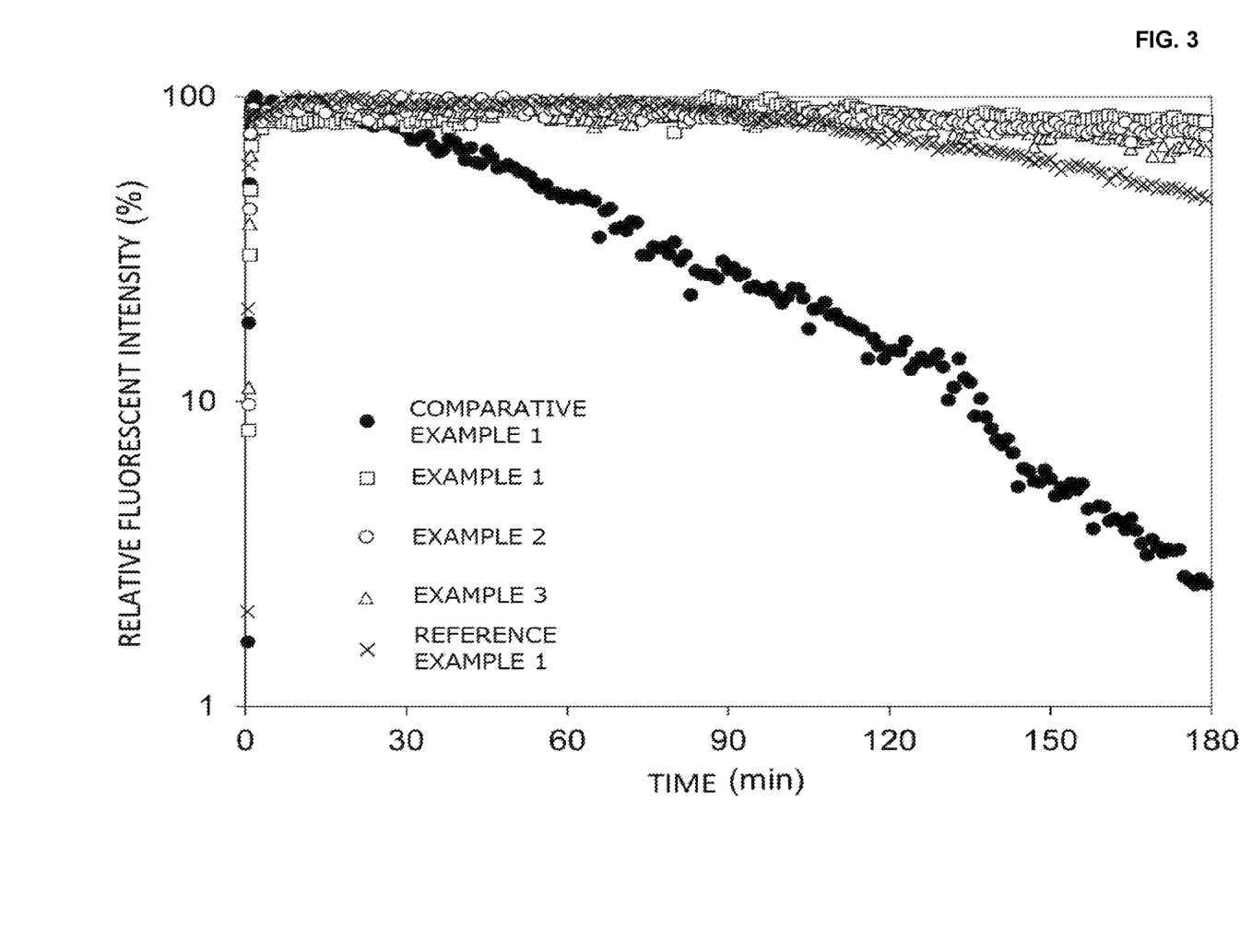
FIG. 3 is a graph that shows the blood retention properties of a nucleic acid that has been complexed with five different block copolymers to form five different uPIC samples.

As shown in FIG. 3, the uPIC solutions (compositions for nucleic acid delivery) of Examples 1 to 3 each exhibited blood retention properties of the nucleic acid that were comparable to the uPIC solution of Reference Example 1. On the other hand, with regard to the uPIC solution of Comparative Example 1, the blood retention properties of the nucleic acid were inferior to the uPIC solutions of Examples 1-3 and Reference Example 1.

The uPICs of the present teachings can be suitably applied in drug delivery systems for nucleic acid therapeutics and the like.

REFERENCE SYMBOL LIST

100 unit-type polyion complex
10 block copolymer
12 cationic poly(amino acid) segment
13, 14 poly(ethylene glycol) segment
20 nucleic acid

The invention claimed is:

1. A unit-type polyion complex, consisting of:
   two molecules of a block copolymer having a poly(ethylene glycol) segment and a cationic poly(amino acid) segment; and one molecule of a nucleic acid electrostatically bound to the two molecules of the block copolymer;

wherein a total quantity of positive charges derived from side chains of the cationic poly(amino acid) segment of the two molecules of the block copolymer in the unit-type polyion complex is between 50-80% of a total quantity of negative charges derived from the one molecule of the nucleic acid, the nucleic acid has a strand length of 10-50 bases, the molecular weight of the poly(ethylene glycol) segment is $40 \times 10^3$ Da or more, and the block copolymer has a binding constant (Ka) for the nucleic acid of $5.0 \times 10^5$ or more.

2. The unit-type polyion complex according to claim 1, wherein the nucleic acid is a double-stranded nucleic acid.

3. The unit-type polyion complex according claim 1, wherein the molecular weight of the poly(ethylene glycol) segment is $60 \times 10^3$ Da or more.

4. The unit-type polyion complex according to claim 1, wherein:

the poly(ethylene glycol) segment is 2-chain branched, and the molecular weight of each of the two poly(ethylene glycol) chains of the poly(ethylene glycol) segment is $20 \times 10^3$ Da or more.

5. The unit-type polyion complex according to claim 1, wherein the cationic poly(amino acid) segment contains ornithine as a constituent amino acid.

6. A composition for nucleic acid delivery, comprising:
the unit-type polyion complex of claim 1; and
at least one additional unassociated molecule of the block copolymer that is capable of forming the unit-type polyion complex, but is in a free state.

7. The composition according to claim 6, wherein a ratio (N/P ratio) of a molar concentration of all amino groups derived from the block copolymer in the composition and a molar concentration of all phosphate groups derived from the nucleic acid in the composition is from 1 to 20.

8. The composition according to claim 7, wherein the nucleic acid is a double-stranded nucleic acid.

9. The composition according to claim 8, wherein the molecular weight of the poly(ethylene glycol) segment is $60 \times 10^3$ Da or more.

10. The composition according to claim 9, wherein:
the poly(ethylene glycol) segment is 2-chain branched, and
the molecular weight of each of the two poly(ethylene glycol) chains of the poly(ethylene glycol) segment is $20 \times 10^3$ Da or more.

11. The composition according to claim 10, wherein the cationic poly(amino acid) segment contains ornithine as a constituent amino acid.

12. The composition according to claim 11, wherein 90% or more of the constituent amino acids of the cationic poly(amino acid) segment are ornithine.

13. The composition according to claim 12, wherein the binding constant (Ka) for the nucleic acid is $1.0 \times 10^6$ or more.

14. The composition according to claim 13, wherein the cationic poly(amino acid) segment contains 9-50 ornithines as a constituent amino acid.

15. The composition according to claim 14, wherein the molecular weight of each of the two poly(ethylene glycol) chains of the poly(ethylene glycol) segment is $35 \times 10^3$ Da or more.

16. The composition according to claim 15, wherein under physiological pH conditions the total quantity of positive charges derived from the ornithine side chains of the two block copolymer molecules in the unit-type polyion complex is 45-80% of the total quantity of negative charges derived from the one molecule of the nucleic acid in the unit-type polyion complex.

17. A method for delivering nucleic acid to tissue of a patient in need thereof, comprising:
administering a therapeutically effective amount of the composition according to claim 6 into the bloodstream of the patient.

18. A unit-type polyion complex consisting of:
two molecules of a block copolymer having a poly(ethylene glycol) segment and a cationic poly(amino acid) segment; and
one molecule of a nucleic acid electrostatically bound to the two molecules of the block copolymer;
wherein:
a total quantity of positive charges derived from side chains of the cationic poly(amino acid) segments of the two molecules of the block copolymer in the unit-type polyion complex is between 50-80% of a total quantity of negative charges derived from the one molecule of the nucleic acid,
the nucleic acid has a strand length of 10-50 bases,
the molecular weight of the poly(ethylene glycol) segment is $40 \times 10^3$ Da or more,
90% or more of the total number of the amino acid residues constituting the cationic polyamino acid segment of both of the two molecules of the block copolymers are basic amino acid residues, and
the block copolymer has a binding constant (Ka) for the nucleic acid of $5.0 \times 10^5$ or more.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: sense strand of siRNA for luciferase including
      dT terminus

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: antisense strand of siRNA for luciferase
      including dT terminus

<400> SEQUENCE: 2
ucgaaguacu cagcguaagt t                                              21
```